United States Patent
Kataoka

(10) Patent No.: US 7,697,764 B2
(45) Date of Patent: Apr. 13, 2010

(54) SIMILAR PATTERN SEARCHING APPARATUS, METHOD OF SIMILAR PATTERN SEARCHING, PROGRAM FOR SIMILAR PATTERN SEARCHING, AND FRACTIONATION APPARATUS

(75) Inventor: Hiromi Kataoka, Nankoku (JP)

(73) Assignees: National University Corporation Kochi University, Kochi-shi (JP); A&T Corporation, Fujisawa-shi (JP)

( * ) Notice: Subject to any disclaimer, the term of this patent is extended or adjusted under 35 U.S.C. 154(b) by 952 days.

(21) Appl. No.: 10/580,252

(22) PCT Filed: Nov. 12, 2004

(86) PCT No.: PCT/JP2004/016841

§ 371 (c)(1),
(2), (4) Date: May 22, 2006

(87) PCT Pub. No.: WO2005/050479

PCT Pub. Date: Jun. 2, 2005

(65) Prior Publication Data

US 2007/0133855 A1    Jun. 14, 2007

(30) Foreign Application Priority Data

Nov. 21, 2003  (JP) .............................. 2003-392845

(51) Int. Cl.
  *G06K 9/00* (2006.01)
  *G01N 33/00* (2006.01)
(52) U.S. Cl. ...................... 382/225; 382/128; 382/134; 435/7.24

(58) Field of Classification Search ................. 382/128, 382/133, 134, 225, 194, 218, 228; 435/6, 435/69.1, 91.2, 320.1, 252.3, 325, 7.24; 430/296, 430/950, 220, 510, 523, 496; 706/25, 20, 706/26; 707/104.1, 4, E17.092, 5, 10, 103 Y; 530/300, 350; 250/492.22; 716/21; 356/39, 356/73; 436/63; 705/26
See application file for complete search history.

(56) References Cited

U.S. PATENT DOCUMENTS 4,617,275 A * 10/1986 Matsuda et al. ................ 436/10

(Continued)

FOREIGN PATENT DOCUMENTS

WO  WO 2005/008254 (A1)    1/2005

OTHER PUBLICATIONS

N. Tatsumi et al., "Practical Use of Automated White Cell Differential," HORIBA Technical Reports, No. 20, 2000, pp. 23-26.

(Continued)

*Primary Examiner*—Sheela C Chawan
(74) *Attorney, Agent, or Firm*—Foley & Lardner LLP

(57) ABSTRACT

Respective components of a leukocyte particle size pattern that includes a plurality of cellular component fractions are separated by performing a mixture density approximation using an EM algorithm, and characteristic parameters of each fraction are clustered. A similarity search with attention paid to a distribution pattern of a cell group of interest is thereby executed. An algorithm capable of doing a highly accurate similarity search from general viewpoints such as a search for the respective cellular components of a leukocyte or a combination of the respective components is developed. In addition, information useful for a diagnosis is provided.

9 Claims, 9 Drawing Sheets

U.S. PATENT DOCUMENTS

| | | | |
|---|---|---|---|
| 4,656,139 A | * | 4/1987 | Matsuda et al. ............... 436/17 |
| 6,246,786 B1 | * | 6/2001 | Nishikiori et al. ........... 382/134 |
| 2006/0190195 A1 | | 8/2006 | Watanabe et al. |

OTHER PUBLICATIONS

H. Kataoka et al., "Construction of Data Mining Assistance System for Leukocyte Particle Size Distribution," Japanese Journal of Clinical Laboratory Automation (JJCLA), vol. 27, No. 4, p. 583.

H. Kataoka et al., "Clustering and 3D Visualization of Leukocyte Scattergrams," Medical Informatics, vol. 22 (Suppl.), 2002, pp. 209-210.

H. Ioki et al., "Clustering of Leukocyte Scattergram in Allergic Diseases," Medical Informatics, vol. 22 (Suppl.), 2002, pp. 211-212.

H. Kataoka et al., "Similarity Search of Protein Electrophoresis Waveform by the Self Organizing Map," Japanese Journal of Clinical Laboratory Automation, vol. 25, No. 4, Aug. 1, 2000, p. 408.

H. Kataoka et al., "Similarity Search of Protein electrophoresis Waveform by the Self Organizing Map and Dynamic Programming Method," Japan Journal of Medical Information, Nov. 23, 2000, No. 20, No. Supplement 2, pp. 394-395.

H. Kataoka et al., "A Data Mining System for Protein Electrophoresis Waveforms," Japanese Journal of Clinical Laboratory Automation, Jun. 1, 2001, vol. 26, No. 3, pp. 170-175.

H. Ioki et al., "Data Mining Case Search by Platelet Scattergram Using Data Mining Method," Japanese Journal of Clinical Laboratory Automation, Aug. 1, 2002, vol. 27, No. 4, p. 584.

H. Kataoka et al., "Similarity Search of Leukocyte Scattergram Based on Mixture Density Approximation and Clustering," $23^{rd}$ JCMI, Nov. 2003, vol. 23, pp. 447-450.

H. Kataoka et al., "A Similarity Wave Data Search Based on Dynamic Programming—SOM," Transactions of Information Processing Society of Japan, Sep. 15, 2001, vol. 42, No. SIG010, pp. 92-99.

Sumio Watanabe, Data Learning Algorithm, ISBN4-320-12005-1, A5, p. 208, 3300, English Translation.

Igor Cadez et al., "A General Probabilistic Framework for Clustering Individuals", Technical Report No. 00-09, Department of Information and Computer Science, University of California, Irvine, 16 pgs., (2000).

Tom Heskes, "Self-organizing maps, vector quantization, and mixture modeling", IEEE Transactions on Neural Networks, vol. XX, No. Y, pp. 1-7(2001).

* cited by examiner

WIDE SIMILARITY DISTANCE RANGE BASED ON Class 351

NARROW SIMILARITY DISTANCE RANGE BASED ON Class 351

SIMILARITY IS VARIABLE IN SEARCH BY DISJUNCTION OF RESPECTIVE CLASSES

CLASSES SORTED IN ASCENDING ORDER OF SIMILARITY DISTANCE

US 7,697,764 B2

SIMILAR PATTERN SEARCHING APPARATUS, METHOD OF SIMILAR PATTERN SEARCHING, PROGRAM FOR SIMILAR PATTERN SEARCHING, AND FRACTIONATION APPARATUS

TECHNICAL FIELD

The present invention relates to a similar-pattern searching apparatus, a similar-pattern searching method, a similar-pattern search program, and a fraction separating apparatus for searching a pattern having a high similarity to a pattern of a test sample from a group including a plurality of patterns.

BACKGROUND ART

Flow cytometry, for example, is a test method capable of clustering a leukocyte into neutrophils, lymphocytes, monocytes, acidophils, and the like within a short period of time. Leukocyte particle size data obtained by the flow cytometry can be classified into various particle size patterns according to a maturation or disease (see Nonpatent Literature 1).

Many facilities have introduced this test as a daily screening test. However, mostly only clustered numerical data is used and the leukocyte particle size data generated in an analyzer is rarely used for clinical diagnosis. There are various reasons for this. For example, the leukocyte particle size data is huge to the extent that it cannot be handled by an external information system. In addition, raw analysis data is only visual searched and it is difficult to investigate the data by a scientific method.

Considering these, the inventor of the present patent application developed a clustering method based on a self-organizing map (SOP) using leukocyte particle size data obtained as a two-dimensional histogram (see Nonpatent Literatures 2 to 4). This clustering method includes recording leukocyte particle size data in a database, and extracting characteristic patterns using the data mining technique, which enables classification that cannot be made based only on the two-dimensional histogram information.

The conventional classification method is executed in the analyzer by using a fraction separating method with troughs of respective fractions set as boundaries. Each of the resultant fractions is used as one piece of numerical data for a diagnosis. However, in this method, the distribution of a plurality of proximate clusters, e.g., stab cells and segmented cells belonging to neutrophils or normal cells and juvenile cells, cannot be separated.

Nonpatent Literature 1: Noriyuki TATSUMI, Izumi TSUDA, Takayuki TAKUBO et al.: "Practical Use of Automated White Cell Differential", HORIBA Technical Reports, No. 20, pp. 23-26, 2000.

Nonpatent Literature 2: Hiromi KATAOKA, Hiromi IOKI, Osamu KONISHI, et al.: "Construction of Data Mining Assistance System for Leukocyte Particle Size Distribution", Japanese Journal of Clinical Laboratory Automation (JJ-CLA), Vol 27, 4, pp. 583, 2002.

Nonpatent Literature 3: Hiromi KATAOKA, Hiromi IOKI, Osamu KONISHI, et al.: "Clustering and 3D visualization of Leukocyte Scattergrams", Medical Informatics 22 (Suppl.), pp. 209-210, 2002.

Nonpatent Literature 4: Hiromi IOKI, Hiromi KATAOKA, Yuka KAWASAKI, et al.: "Clustering of Leukocyte Scattergram in Allergic Diseases", Medical Informatics 22 (Suppl.), pp. 211-212, 2002.

DISCLOSURE OF INVENTION

Problem to be Solved by the Invention

The present invention has been made to solve the problems in the conventional technology. It is an object of the present invention to provide a similar-pattern searching apparatus, a similar-pattern searching method, a similar-pattern search program, and a fraction separating apparatus capable of highly accurately doing a similarity search for a pattern having a high similarity to a pattern of a test sample from a group including a plurality of patterns, and providing information useful for a diagnosis.

Means for Solving Problem

To solve the above problems and to achieve the objects, according to an aspect of the present invention, a similar-pattern searching apparatus for searching a pattern having a high similarity to a pattern of a test sample from a group including a plurality of patterns includes a storage unit that stores a class map generated by selecting model parameters that characterize a plurality of component fractions included in each of the patterns, and by clustering the patterns; and a similar-pattern searching unit that selects a class similar to a component fraction included in the pattern of the test sample from the class map.

According to the above aspect, a plurality of patterns are clustered to generate the class map using the model parameters that characterize a plurality of component fractions included in each of the patterns. The class similar to the component fraction included in the pattern of the test sample is selected from the class map, and subjected to a highly accurate similar search.

According to another aspect of the present invention, the patterns are one-dimensional or multi-dimensional patterns. According to the aspect, the one-dimensional or multi-dimensional patterns are subjected to the highly accurate similarity search.

According to still another aspect of the present invention, the patterns are leukocyte particle size patterns, protein electrophoretic waveforms, or blood cell histograms. According to the aspect, the leukocyte particle size patterns, the protein electrophoretic waveforms, or the blood cell histograms are subjected to the highly accurate similarity search.

According to still another aspect of the present invention, a similar-pattern searching method of searching a pattern having a high similarity to a pattern of a test sample from a group including a plurality of patterns includes a class-map generating step of selecting model parameters that characterize a plurality of component fractions included in each of the patterns, clustering the patterns, and generating a class map; a storage step of storing the class map generated at the class-map generating step; and a similar-pattern searching step of selecting a class similar to a component fraction included in the pattern of the test sample from the class map.

According to the above aspect, a plurality of patterns are clustered to generate the class map using the model parameters that characterize a plurality of component fractions included in each of the patterns. The class similar to the component fraction included in the pattern of the test sample is selected from the class map, and subjected to a highly accurate similar search.

According to still another aspect of the present invention, a similar-pattern search program that realizes on a computer a similar-pattern searching method of searching a pattern having a high similarity to a pattern of a test sample from a group including a plurality of patterns, causes the computer to execute a class-map generating process of selecting model parameters that characterize a plurality of component fractions included in each of the patterns, clustering the patterns, and generating a class map; a storage process of storing the class map generated at the class-map generating process; and a similar pattern search step of selecting a class similar to a component fraction included in the pattern of the test sample from the class map.

According to the above aspect, a plurality of patterns are clustered to generate the class map using the model parameters that characterize a plurality of component fractions included in each of the patterns. The class similar to the component fraction included in the pattern of the test sample is selected from the class map, and subjected to a highly accurate similar search.

According to still another aspect of the present invention, a similar-pattern searching apparatus for searching a leukocyte particle size pattern having a high similarity to a leukocyte particle size pattern of a test sample from a group including a plurality of leukocyte particle size patterns, each of the leukocyte particle size patterns including a plurality of cellular component fractions includes a primary clustering unit that clusters the leukocyte particle size patterns obtained by a measurement while applying a self-organizing map to the leukocyte particle size patterns, and that generates a primary class map; a first-parameter determining unit that executes an EM algorithm for the respective leukocyte particle size patterns included in the primary class map using predetermined initial values, thereby determining first-mixture-distribution model parameters including the number of cellular components contained in each of the patterns, and an average, a variance, and a density of each of the cellular components; a second-parameter determining unit that executes the EM algorithm for the respective leukocyte particle size patterns using the first-mixture-distribution model parameters as the initial values, thereby determining second mixture distribution model parameters including the number of the cellular components contained in each of the leukocyte particle size patterns, and the average, the variance, and the density of each cellular component; a secondary clustering unit that clusters the respective leukocyte particle size patterns while applying the self-organizing map to the first mixture distribution model parameters, and that generates a secondary class map; an inter-class distance master generator that calculates similarity distances between all combinations of respective classes included in the secondary class map, and that generates an inter-class distance master in which the combinations of the classes correspond to the respective inter-class similarity distances; a storage unit that stores the secondary class map and the inter-class distance master; a class determining unit that determines a class belonging to each of cellular component fractions included in the leukocyte particle size pattern of the test sample from the secondary class map; and a similar-pattern searching unit that detects, as a similar class, a class which similarity distance from the class determined by the class determining unit is equal to or smaller than a predetermined threshold, from the inter-class distance master, and that determines a leukocyte particle size pattern included in the similar class as the pattern having the high similarity to the leukocyte particle size pattern of the test sample.

According to the above aspect, the respective components included in each of the leukocyte particle sizes are separated by the EM algorithm using the initial values determined by using the self-organizing map. In addition, the leukocyte particle size patterns are clustered again using the self-organizing map. The secondary class map and the inter-class distance master are thereby constructed.

According to still another aspect of the present invention, a similar-pattern searching method of searching a leukocyte particle size pattern having a high similarity to a leukocyte particle size pattern of a test sample from a group including a plurality of leukocyte particle size patterns, each of the leukocyte particle size patterns including a plurality of cellular component fractions includes a primary clustering step of clustering the leukocyte particle size patterns obtained by a measurement while applying a self-organizing map to the leukocyte particle size patterns, and generating a primary class map; a first-parameter determining step of executing an EM algorithm for the respective leukocyte particle size patterns included in the primary class map using predetermined initial values, thereby determining first-mixture-distribution model parameters including the number of cellular components contained in each of the patterns, and an average, a variance, and a density of each of the cellular components; a second-parameter determining step of executing the EM algorithm for the respective leukocyte particle size patterns using the first-mixture-distribution model parameters as the initial values, thereby determining second mixture distribution model parameters including the number of the cellular components contained in each of the leukocyte particle size patterns, and the average, the variance, and the density of each cellular component; a secondary clustering step of clustering the respective leukocyte particle size patterns while applying the self-organizing map to the first mixture distribution model parameters, and generating a secondary class map; an inter-class distance master generating step of calculating similarity distances between all combinations of respective classes included in the secondary class map, and generating an inter-class distance master in which the combinations of the classes correspond to the respective inter-class similarity distances; a storing step of storing the secondary class map and the inter-class distance master; a class determining step of determining a class belonging to each of cellular component fractions included in the leukocyte particle size pattern of the test sample from the secondary class map; and a similar-pattern searching step of detecting, as a similar class, a class which similarity distance from the class determined at the class determining step is equal to or smaller than a predetermined threshold, from the inter-class distance master, and determining a leukocyte particle size pattern included in the similar class as the pattern having the high similarity to the leukocyte particle size pattern of the test sample.

According to the above aspect, the respective components included in each of the leukocyte particle sizes are separated by the EM algorithm using the initial values determined by using the self-organizing map. In addition, the leukocyte particle size patterns are clustered again using the self-organizing map. The secondary class map and the inter-class distance master are thereby constructed.

According to still another aspect of the present invention, a similar-pattern search program that realizes on a computer a similar-pattern searching method of searching a leukocyte particle size pattern having a high similarity to a leukocyte particle size pattern of a test sample from a group including a plurality of leukocyte particle size patterns, each of the leukocyte particle size patterns including a plurality of cellular component fractions, causes the computer to execute a primary clustering process of clustering the leukocyte particle size patterns obtained by a measurement while applying a self-organizing map to the leukocyte particle size patterns, and generating a primary class map; a first-parameter determining process of executing an EM algorithm for the respective leukocyte particle size patterns included in the primary class map using predetermined initial values, thereby determining first-mixture-distribution model parameters including the number of cellular components contained in each of the patterns, and an average, a variance, and a density of each of the cellular components; a second-parameter determining process of executing the EM algorithm for the respective leukocyte particle size patterns using the first-mixture-distribution model parameters as the initial values, thereby determining second mixture distribution model parameters including the number of the cellular components contained in each of the leukocyte particle size patterns, and the average, the variance, and the density of each cellular component; a secondary clustering process of clustering the respective leukocyte particle size patterns while applying the self-organizing map to the first mixture distribution model parameters, and generating a secondary class map; an inter-class distance master generating process of calculating similarity distances between all combinations of respective classes included in the secondary class map, and generating an inter-class distance master in which the combinations of the classes correspond to the respective inter-class similarity distances; a storing process of storing the secondary class map and the inter-class distance master; a class determining process of determining a class belonging to each of cellular component fractions included in the leukocyte particle size pattern of the test sample from the secondary class map; and a similar-pattern searching process of detecting, as a similar class, a class which similarity distance from the class determined at the class determining process is equal to or smaller than a predetermined threshold, from the inter-class distance master, and determining a leukocyte particle size pattern included in the similar class as the pattern having the high similarity to the leukocyte particle size pattern of the test sample.

According to the above aspect, the respective components included in each of the leukocyte particle sizes are separated by the EM algorithm using the initial values determined by using the self-organizing map. In addition, the leukocyte particle size patterns are clustered again using the self-organizing map. The secondary class map and the inter-class distance master are thereby constructed.

According to still another aspect of the present invention, a cellular-component-fraction separating apparatus for separating a plurality of cellular component fractions included in a leukocyte particle size pattern includes a primary clustering unit that clusters a plurality of leukocyte particle size patterns, which are obtained by measurement, while applying a self-organizing map to the leukocyte particle size patterns, and that generates a primary class map; a parameter determining unit that executes an EM algorithm for the respective leukocyte particle size patterns included in the primary class map using predetermined initial values, thereby determining mixture distribution model parameters including the number of cellular components contained in each of the patterns, and an average, a variance, and a density of each of the cellular component fractions; and a fraction separating unit that executes the EM algorithm for the respective leukocyte particle size patterns using the mixture distribution model parameters as the initial values, thereby separating the cellular component fractions included in each of the leukocyte particle size patterns.

According to the above aspect, self-organizing map (SOM) is applied to determine the initial values of the EM algorithm.

EFFECT OF THE INVENTION

The similar-pattern searching apparatus according to one aspect clusters a plurality of patterns to generate the class map using the model parameters that characterize a plurality of component fractions included in each of the patterns. In addition, the apparatus selects the class similar to the component fraction included in the pattern of the test sample from the class map. It is, therefore, advantageously possible to highly accurately search a pattern having a high similarity to the pattern of the test sample from the group including a plurality of patterns. In addition, it is advantageously possible to provide information useful for a diagnosis.

The similar-pattern searching apparatus according to another aspect uses the one-dimensional or multi-dimensional patterns as the patterns. It is, therefore, advantageously possible to highly accurately search a pattern having a high similarity to the one-dimensional or multi-dimensional pattern of the test sample.

The similar-pattern searching apparatus according to still another aspect uses the leukocyte particle size patterns, the protein electrophoretic waveforms, or the blood cell histograms as the patterns. It is, therefore, advantageously possible to highly accurately search a pattern having a high similarity to the leukocyte particle size pattern or a pattern of the protein electrophoretic waveforms or the blood cell histograms.

With the similar-pattern searching method according to still another aspect a plurality of patterns are clustered to generate the class map using the model parameters that characterize a plurality of component fractions included in each of the patterns. In addition, the class similar to the component fraction included in the pattern of the test sample is selected from the class map. It is, therefore, advantageously possible to highly accurately search a pattern having a high similarity to the pattern of the test sample from the group including a plurality of patterns. In addition, it is advantageously possible to provide information useful for a diagnosis.

The similar-pattern search program according to still another aspect clusters a plurality of patterns to generate the class map using the model parameters that characterize a plurality of component fractions included in each of the patterns. In addition, the similar-pattern search program selects the class similar to the component fraction included in the pattern of the test sample from the class map. It is, therefore, advantageously possible to highly accurately search a pattern having a high similarity to the pattern of the test sample from the group including a plurality of patterns. In addition, it is advantageously possible to provide information useful for a diagnosis.

The similar-pattern searching apparatus according to still another aspect separates the respective components included in each of the leukocyte particle sizes by the EM algorithm using the initial values determined by using the self-organizing map. In addition, the apparatus clusters again the leukocyte particle size patterns using the self-organizing map. The apparatus thereby constructs the secondary class map and the inter-class distance master. It is, therefore, advantageously possible to arbitrarily select the similarities of the search target.

Conventionally, the particle size data of two-dimensional histograms is directly used to perform clustering using self-organizing map (SOM). Due to this, a similarity search with attention paid to partial similarities of interest cannot be done for the respective components of the leukocyte. According to the present invention, by performing a mixture density approximation using an EM algorithm to separate the respective components, and further by clustering characteristic parameters of respective fractions, it is possible to perform the similarity search with attention paid to the distribution pattern of the cell group of interest.

With the similar-pattern searching method according to still another aspect, the respective components included in each of the leukocyte particle sizes are separated by the EM algorithm using the initial values determined by using the self-organizing map. In addition, the leukocyte particle size patterns are clustered again using the self-organizing map. The secondary class map and the inter-class distance master are thereby constructed. It is, therefore, advantageously possible to arbitrarily select the similarities of the search target.

The similar-pattern search program according to still another aspect separates the respective components included in each of the leukocyte particle sizes by the EM algorithm using the initial values determined by using the self-organizing map. In addition, the similar-pattern search program clusters again the leukocyte particle size patterns using the self-organizing map. The similar-pattern search program thereby constructs the secondary class map and the inter-class distance master. It is, therefore, advantageously possible to arbitrarily select the similarities of the search target.

The fraction separating apparatus according to still another aspect applies the self-organizing map (SOM) to determination of the initial values of the EM algorithm. It is, therefore, advantageously possible to solve the problem of convergence of the marginal likelihood on the local maximum.

EXPLANATIONS OF LETTERS OR NUMERALS

Figure 1:
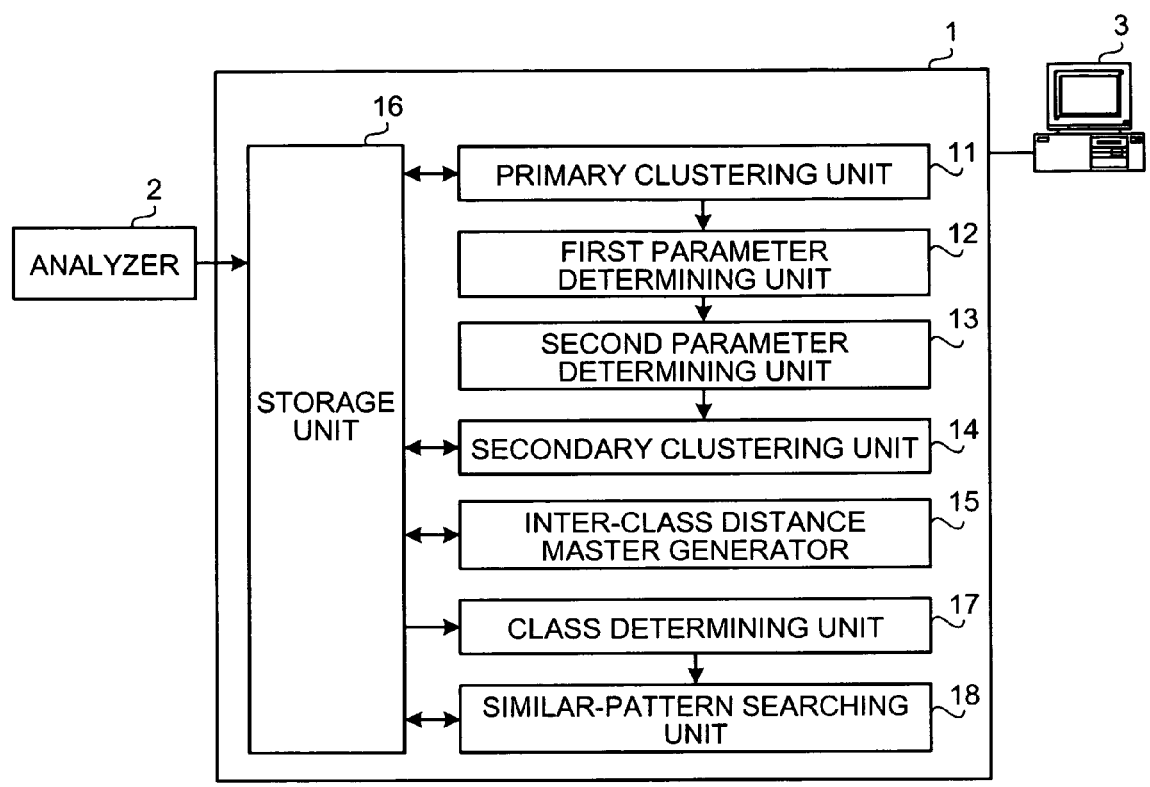
FIG. 1 is a block diagram of a similar-pattern searching apparatus 1 according to an embodiment of the present invention.

1 Similar pattern search apparatus
11 Primary clustering unit
12 First parameter determining unit
13 Second parameter determining unit
14 Secondary clustering unit
15 Inter-class distance master generator
16 Memory
17 Class determining unit
18 Similar pattern search unit
2 Analyzer
3 External input and output apparatus

BEST MODE(S) FOR CARRYING OUT THE INVENTION

Exemplary embodiments of a similar-pattern searching apparatus, a similar-pattern searching method, a similar-pattern search program, and a fraction separating apparatus according to the present invention will be explained hereinafter in detail with reference to the accompanying drawings. The present invention is not limited to the embodiments. Constituent elements in the embodiments below include elements that persons skilled in the art can easily assume or that are substantially the same. While a leukocyte particle size pattern is explained as an example in the embodiments, the present invention is not limited thereto.

After performing intensive research, the inventor of the present patent application discovered that a similarity search can be done with attention paid to a distribution pattern of a cell group of interest by performing a mixture density approximation on cellular components contained in a leukocyte particle size pattern using an EM algorithm to separate the respective components, and further by clustering characteristic parameters of respective fractions. Based on this knowledge, the inventor eventually made the present invention.

Generally, the EM algorithm has the following problems. A convergent point largely depends on initial conditions and a local maximum of a marginal likelihood is unavoidable. Namely, a phenomenon of convergence of the marginal likelihood on a low-level local solution occurs depending on initial values. The embodiments of the present invention are intended to solve the problem of the convergence of the marginal likelihood on the local maximum by calculating initial values of respective classes based on a result of clustering entire leukocyte particle size data by self-organizing map (SOM) in advance. According to the embodiments, an algorithm capable of doing a high speed similarity search from general viewpoints such as a search for the respective cellular components of the leukocyte or a combination of the respective components is developed. In addition, information useful for a diagnosis is provided.

An embodiment of the present invention will be explained hereinafter. FIG. 1 is a block diagram of a similar-pattern searching apparatus 1 according to the embodiment of the present invention. The similar-pattern searching apparatus 1 includes a primary clustering unit 11, a first parameter determining unit 12, a second parameter determining unit 13, a secondary clustering unit 14, an inter-class distance master generator 15, a storage unit 16, a class determining unit 17, and a similar-pattern searching unit 18.

According to the present embodiment, respective components can be separated by performing a mixture density approximation using the EM algorithm, and a similarity search with attention paid to a distribution pattern of a cell group of interest can be performed by clustering characteristic parameters of each of resultant fractions.

The EM algorithm is constituted by two processing algorithms, i.e., an Expectation step (E-step) and a Maximization step (M-step). By repeating operations these two steps by changing the parameters until a convergence is obtained a maximal point of a maximum likelihood estimated values can be acquired. The E-step includes calculating conditional expectation values of a logarithmic likelihood, while the M-step includes maximizing the conditional expectation values.

A dataset and an approximation model used in this embodiment are as follows.

Data type: Two-dimensional histograms
Model: Normal mixture model
Parameters: Average, variance, and density Generally, the EM algorithm has the following problems. A convergent point largely depends on initial conditions and a local maximum of a marginal likelihood is unavoidable. Namely, the phenomenon of convergence of the marginal likelihood on a low-level local solution occurs depending on initial values. The embodiments of the present invention are intended to solve the problem of the convergence of the marginal likelihood on the local maximum by calculating initial values of respective classes based on a result of clustering entire leukocyte particle size data by the SOM in advance.

An analyzer 2 measures data on the two-dimensional histograms of leukocyte particle sizes. The similar-pattern searching apparatus 1 obtains the data from the analyzer 2 and stores it in the storage unit 16.

The primary clustering unit 11 clusters patterns of a plurality of leukocyte particle size patterns obtained by a measurement while applying the SOM to the patterns, and generate a primary class map.

The first parameter determining unit 12 executes the EM algorithm using predetermined initial values for the respective patterns included in the primary class map. The first parameter determining unit 12 thereby determines first mixture distribution model parameters constituted by the number of cellular components contained in each leukocyte particle size pattern, and an average, a variance, and a density of each cellular component.

The second parameter determining unit 13 executes the EM algorithm for the respective measured leukocyte particle size patterns with the first mixture distribution model parameters assumed as the initial values. The second parameter determining unit 13 thereby determines second mixture distribution model parameters constituted by the number of cellular components contained in each leukocyte particle size pattern, and an average, a variance, and a density of each cellular component.

The secondary clustering unit 14 clusters the second mixture distribution model parameters while applying the SOC to the patterns, and generates a secondary class map. In the present embodiment, the SOM is used for the clustering. Alternatively, K-mean clustering or the other clustering can be performed.

The inter-class distance master generator 15 calculates similarity distances between all combinations of the classes included in the secondary class map. In addition, the inter-class distance master generator 15 generates an inter-class master in which the combinations of classes correspond to the respective inter-class distances.

The storage unit 16 stores therein such data as the two-dimensional histogram data on the leukocyte particle size patterns measured by the analyzer 2, the secondary class map data generated by the secondary clustering unit 14, and the inter-class distance master data generated by the inter-class distance master generator 15.

The class determining unit 17 determines a class belonging to each cellular component fraction contained in a leukocyte particle size pattern of a test sample from the secondary class map.

The similar-pattern searching unit 18 detects, as a similar class, a class, of which similarity distance from the class determined at the class determination step is equal to or smaller than a threshold, from the inter-class distance master. In addition, the similar-pattern searching unit 18 determines a leukocyte particle size pattern included in the similar class as a pattern having a high similarity to the leukocyte particle size pattern of the test sample. In the present embodiment, in determining the similarity, the inter-class distance is used. However, a similarity evaluation criterion (cluster evaluation criterion) is not limited to the inter-class distance. Alternatively, a distance from the center of gravity of a cluster, an intra-cluster distance or the like can be used.

An external input and output apparatus 3 transmits user-input parameters, similar pattern search conditions and the like input to the similar-pattern searching apparatus 1. In addition, the external input and output apparatus 3 outputs the similar patterns hit in the similar-pattern searching apparatus 1 on a screen.

Figure 2:
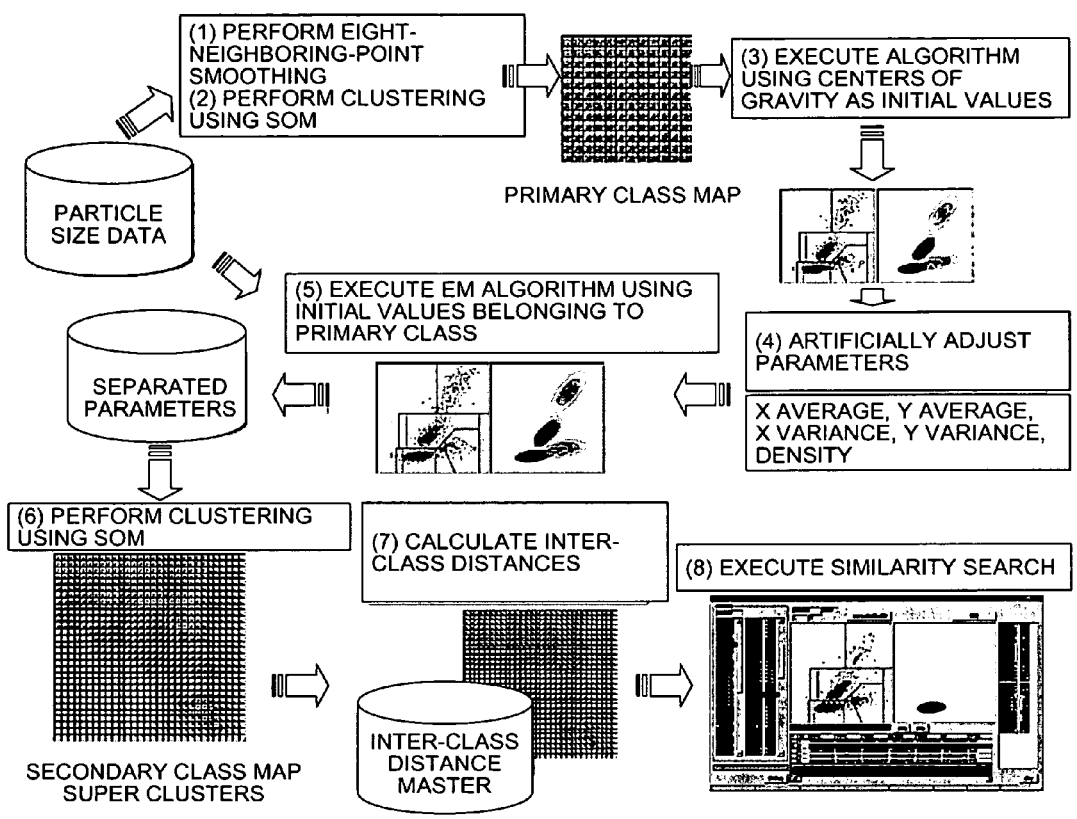
FIG. 2 is a flowchart of a process performed by the similar-pattern searching apparatus 1.

FIG. 2 is a flowchart of a process performed by the similar-pattern searching apparatus 1 according to the present embodiment. It is noted that an instance of processing data of two-dimensional histograms 128×128 for LMNE channels of 8,800 ordinary patient test samples analyzed by an automatic blood cell counter PENTRA120 (manufactured by HORIBA, Ltd.) with eight bits per test sample will be explained as a specific example of the process.

(1) Generation of the primary class map for determination of initial values

The similar-pattern searching apparatus 1 clusters data obtained by subjecting the two-dimensional histogram data output from the analyzer 2 to eight-neighboring-point smoothing using a SOM including input layers 128×128 (16, 384 neurons) and competitive layers 12×12 (units), thereby obtaining 144 patterns. The similar-pattern searching apparatus 1 determines the 144 patterns as the primary class map. As learning parameters for the SOM, a neighboring distance is set to four and a learning rate is set to 0.3. Furthermore, for each pattern on this primary class map, 4×4 or 16 divided regions are set, and the center of gravity of a two-dimensional histogram of each region is calculated. Using the centers of gravities as initial values, a mixture model is separated by the EM algorithm. The calculation is made on assumption that a distribution model of each fraction is a normal distribution. Obtained mixture distribution model parameters (the number of components, and an average, a variance, and a density of each component) are artificially adjusted. Temporary parameters are thereby determined.

(2) Mixture distribution approximation by the EM algorithm

The mixture distribution approximation by the EM algorithm can be carried out using a technique explained in Sumio Watanabe: Data Learning Algorithm, Kyoritu Shuppan Co., Ltd., 2001; Igor V. Cadez, Scott Gaffney, Padharaic Smyth: "A General Probabilistic Framework for Clustering Individuals and Objects", Knowledge Discovery and Data Mining, pp. 140-149, 2000, or the like.

Specifically, a class having a highest similarity to the primary map is searched from the two-dimensional histogram data on each test sample. The EM algorithm is executed using mixture distribution model parameters for the searched class, thereby separating the particle size components. The same process is executed for particle size data on all test samples and individual mixture distribution model parameters are calculated.

(3) The secondary class map using the SOC with mixture distribution parameters used as inputs can be generated by using a technique explained in Tom Heskes: "Self-organizing maps, vector quantization, and mixture modeling", IEEE Transactions on Neural Networks, 12, pp. 1299-1305, 2001. or the like.

The data is clustered while adding, to each input layer, actual number mixture distribution model parameters constituted by six parameters, i.e., an X average, a Y average, a Y covariance matrix, an XY covariance matrix, and a density, using a SOM having competitive layers 30×30 (units), a neighboring distance of 10, and a learning rate of 0.3. This clustering result is used as a secondary class map for a similarity search. At this time, similarity distances between all combinations of the classes are calculated and registered in the inter-class distance master.

(4) Similarity search

A class belonging to each fraction of each test sample is obtained from the secondary class map, the inter-class distance master is read, and a threshold is determined according to a purpose of the search. Class groups that coincide with the conditions are searched. By making the threshold variable, an intensity of the similarity in the search can be arbitrarily selected. Furthermore, by searching the class group in a region included in the threshold under disjunction conditions, the similarity search is realized. To search a general pattern of the respective fractions, the search is done by conjunction of classes belonging to the respective fractions.

Figure 3:
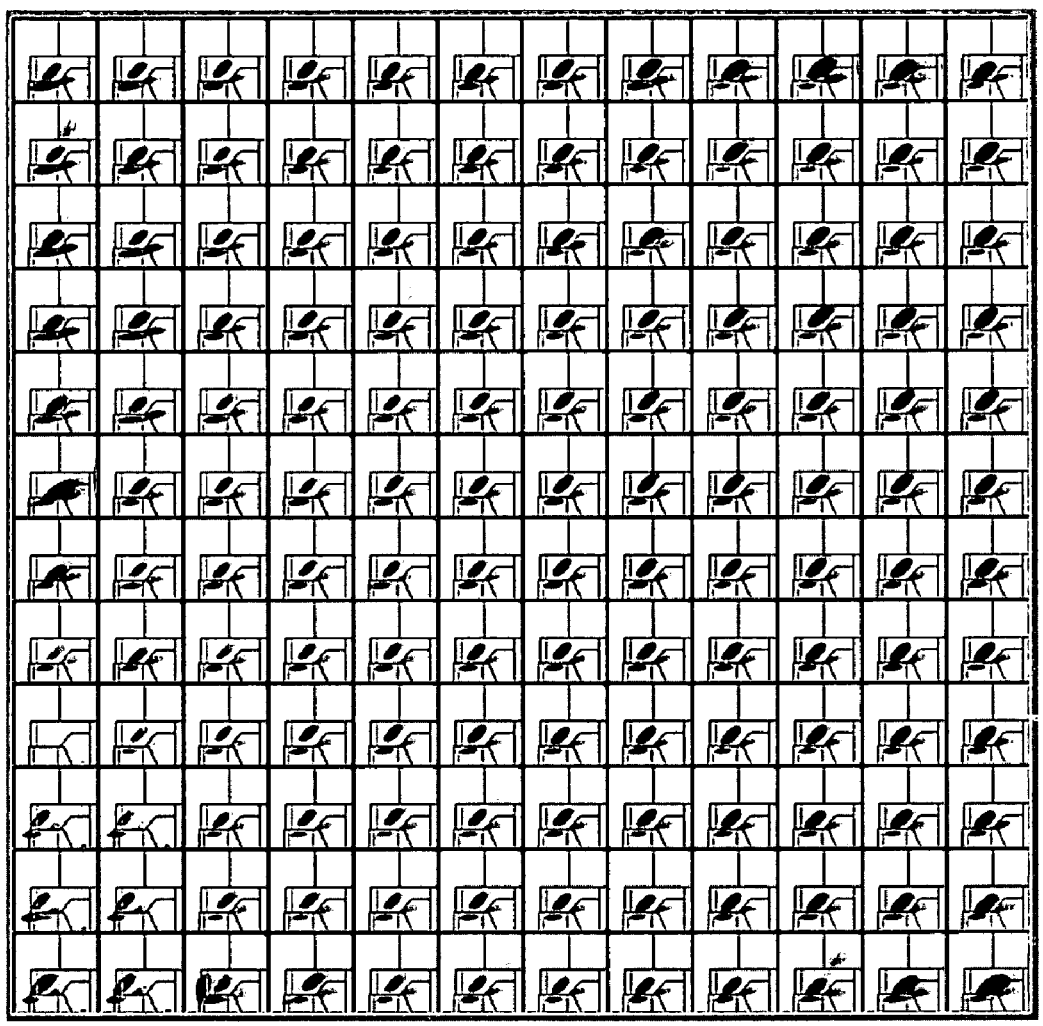
FIG. 3 is an example a primary class map obtained as a result of primary clustering using a self-organizing map (SOM)

FIG. 3 is a view of a result of primary clustering using the SOM. FIG. 3 displays an inside of 12×12 competitive layers. A result of clustering the entire leukocyte particle size patterns to 144 clusters is obtained.

Figure 4:
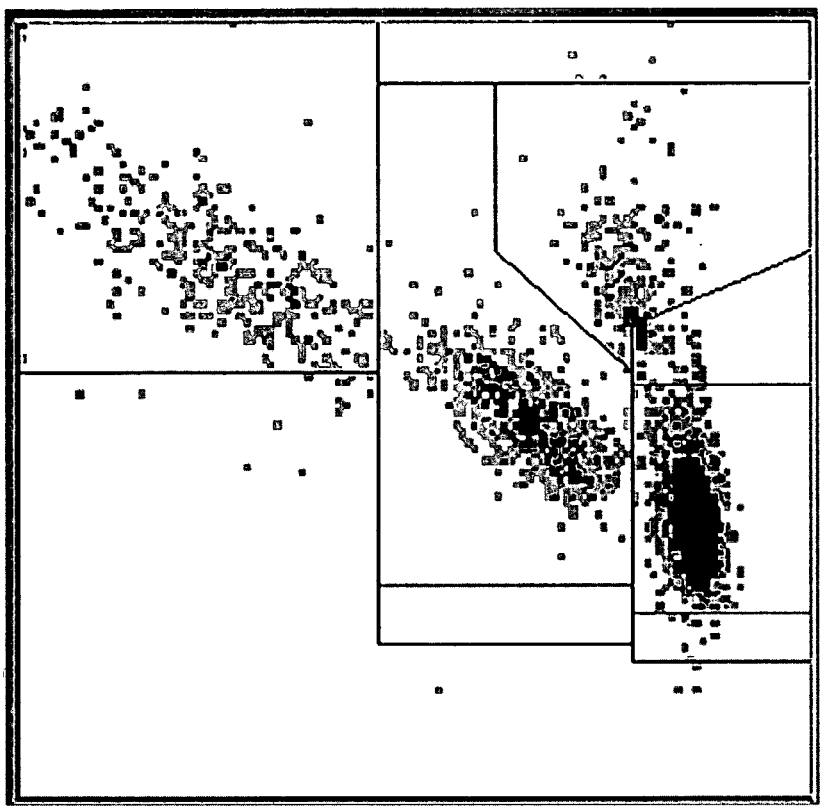
FIG. 4 depicts a two-dimensional histogram of original particle size data (upper view), and, depicts a redrawn and modeled two-dimensional histogram obtained by combining respective fraction components using obtained mixture distribution parameters (lower view)
Figure 4:

An upper view of FIG. 4 depicts a two-dimensional histogram of original particle size data, where symbol + indicates an initial value and a symbol × indicates a path on which the most likelihood search is executed by the EM algorithm and a convergent point. A lower view of FIG. 4 depicts a redrawn and modeled two-dimensional histogram obtained by combining the respective fraction components using the obtained mixture distribution parameters.

Figure 5:
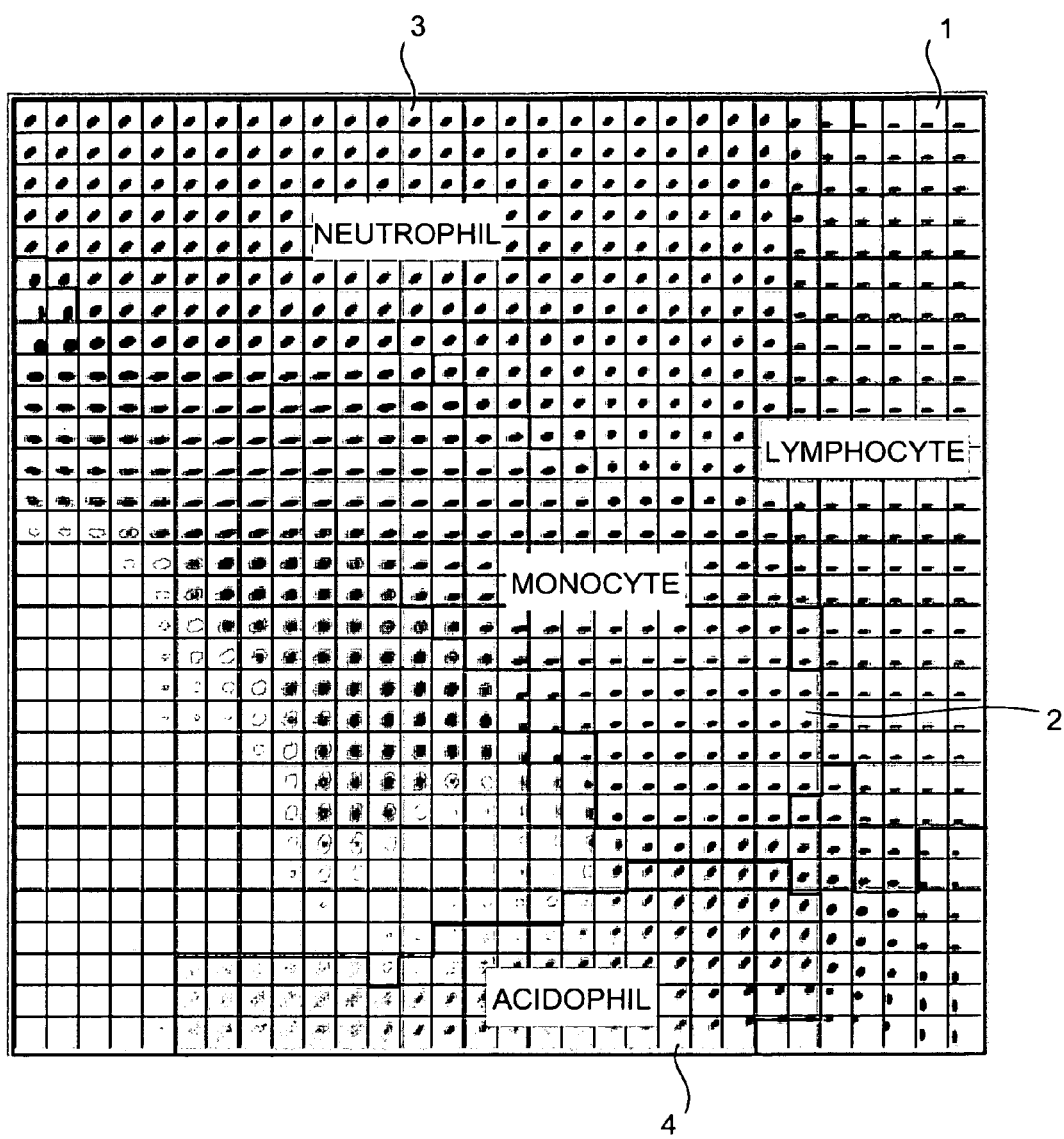
FIG. 5 is an example a secondary class map obtained as a result of clustering respective mixture distribution model parameters obtained by an EM algorithm using the SOM.

FIG. 5 is a result of clustering the respective mixture distribution model parameters obtained by the EM algorithm using the SOM. An elliptic component drawn in red indicates a cellular component fraction. Similar patterns are arranged around the elliptic component. As can be understood from FIG. 5, various patterns are present for the respective cell groups. Distributions of lymphocytes, monocytes, neutrophils, and acidophils are obtained in a pink region 1, a yellow region 2, a sky blue region 3, and a purple region 4, respectively. The cells are clustered into four cell groups literally LMNE channels. Furthermore, blood platelets are mapped on a white region distributed below the lymphocytes, distributions considered to be abnormal cells are mapped on boundary regions between the other white regions and the respective cell groups. The cell groups shown in FIGS. 5 and 6 will be referred to by their sequential numbers in raster direction with an upper left corner defined as Class 0 and a lower right corner defined as Class 899.

Figure 6:
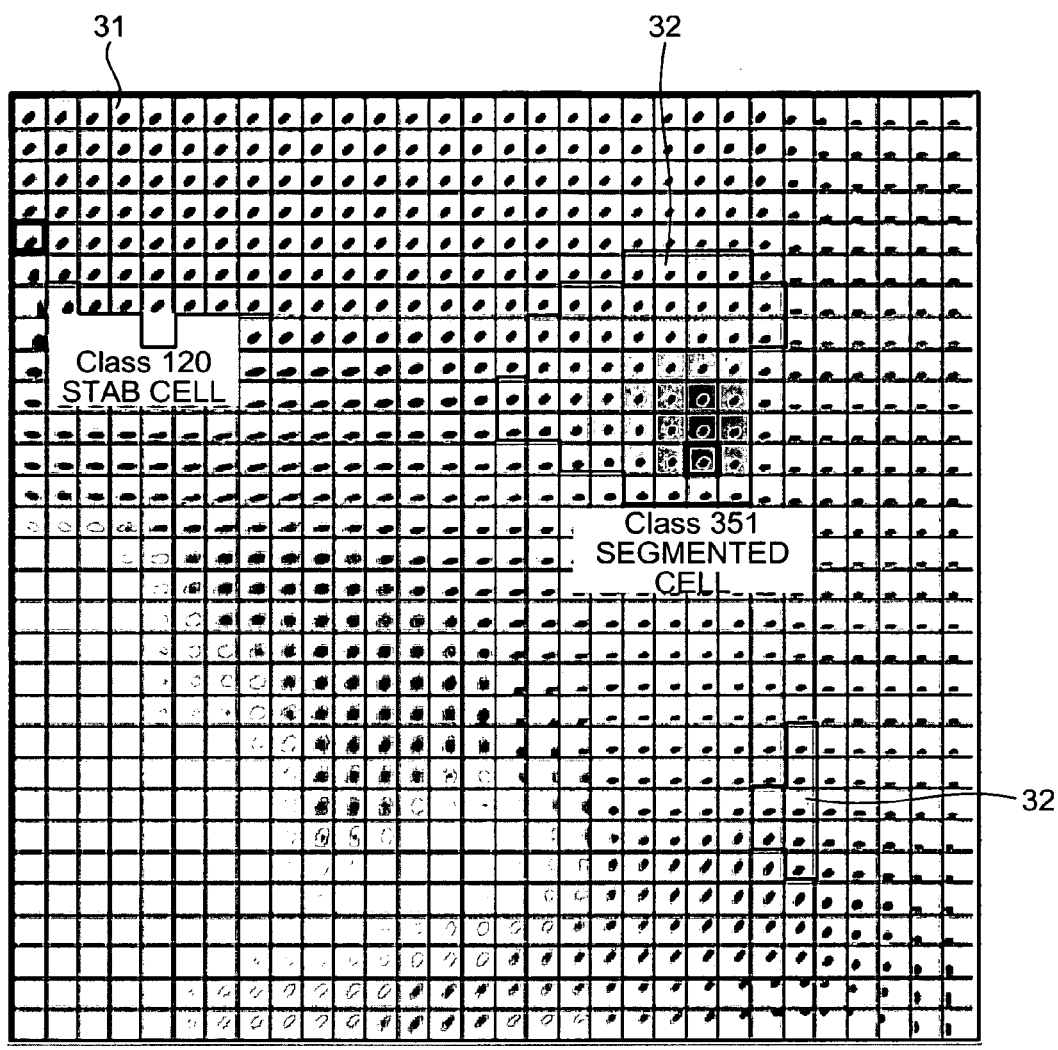
FIG. 6 is a distribution chart of stab cells and segmented cells distributed in a neutrophil region.

FIG. 6 is a distribution chart of stab cells and segmented cells distributed in the neutrophil region. According to a result of visual classification by a microscope, Class 120 is a class including more stab cells than any other class and Class 351 is a class including more segmented cells than any other class. A yellow gradation region 31 (left) shows a distribution of expressing similarity distance patterns centering around the Class 120 including the most stab cells conspicuously moving leftward by color intensities. In addition, a blue gradation region 32 (right) shows patterns centering around the Class 351 including the most segmented cells.

Figure 7:
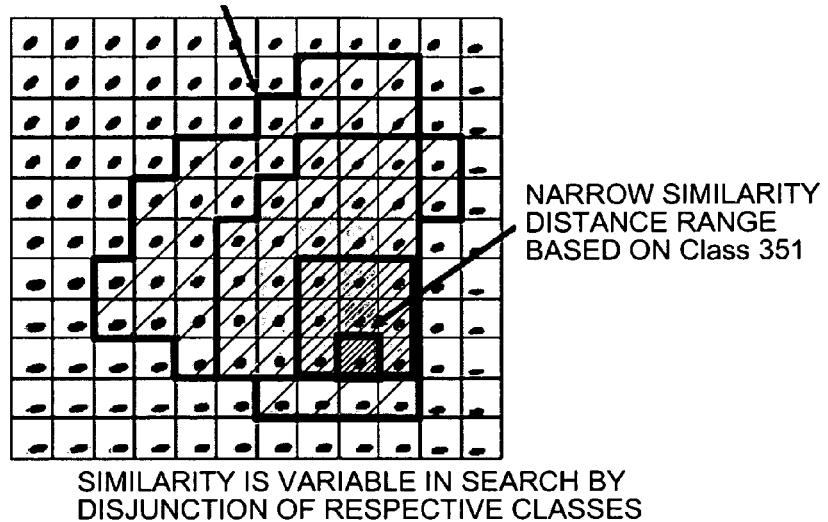
FIG. 7 is an enlarged view of a segmented cell distribution based on Class 351.

FIG. 7 is an enlarged view of the segmented cell distribution based on the Class 351. To do a similarity search in a wide range, the classes in a region surrounded by a red line are searched. To do a search on high similarity cells, classes in a region surrounded by a green line or a blue line are searched. By doing so, search targets can be narrowed down.

Figure 8:
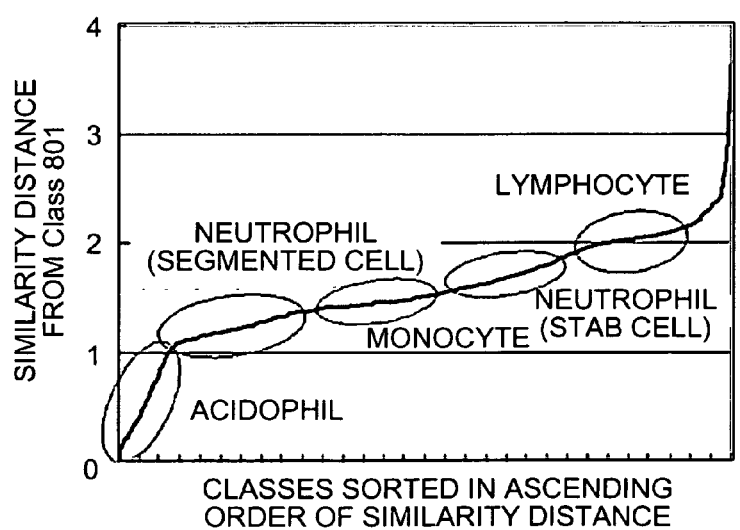
FIG. 8 is a chart of plotting distances of respective classes from Class 801 of acidophils.

Visual boundary surfaces of the stab cells (Class 120) and the segmented cells (Class 351) shown in FIG. 6 are combined by smooth gradations, which indicates that a similarity boundary is unclear. This suggests that the stab cells and the segmented cells equally belong to neutrophils and similarities can be, therefore, clustered on the map according to differentiation degrees of cells. On the other hand, clear boundary surfaces with fewer gradations are observed on a boundary between the segmented cells in the Class 351 and the lymphocyte region. This suggests that these cell groups can be clearly separated on the map. FIG. 8 is a chart of plotting distances of the respective classes from the Class 801 of the acidophils. In FIG. 8, the vertical axis indicates the distance from the Class 801 and the horizontal axis indicates classes sorted in an ascending order of distance. As can be seen from FIG. 8, acidophils are distributed in a range at a distance equal to or smaller than one, and similarities of search targets can be changed by making a threshold of the distance variable. In addition, an interesting result is obtained that a stepped curve is obtained for the respective cell groups and that the stab cells and the segmented cells of the neutrophils are divided by the monocyte. This has a tendency that various patterns are obtained according to the cells based on which the distances of the cells are plotted.

The similarity search system capable of arbitrarily changing a similarity criterion for similarities of the individual components of the leukocyte or a combined similarity of the components is constructed. In the EM algorithm, the initial values are determined by the patterns clustered using the SOM in advance, whereby a correct convergence result is obtained. The stab cells cannot be separated from the segmented cells by the flow cytometry in a clinical test region. However, they can be easily separated by using the method according to the embodiment, and the system that provides useful information for the diagnosis and treatment can be constructed.

One embodiment of the present invention has been explained in detail with reference to the drawings. However, specific examples of the configuration are not limited to this embodiment. Even design changes and the like within the scope of the concept of the present invention are also included in the present invention.

Figure 9:
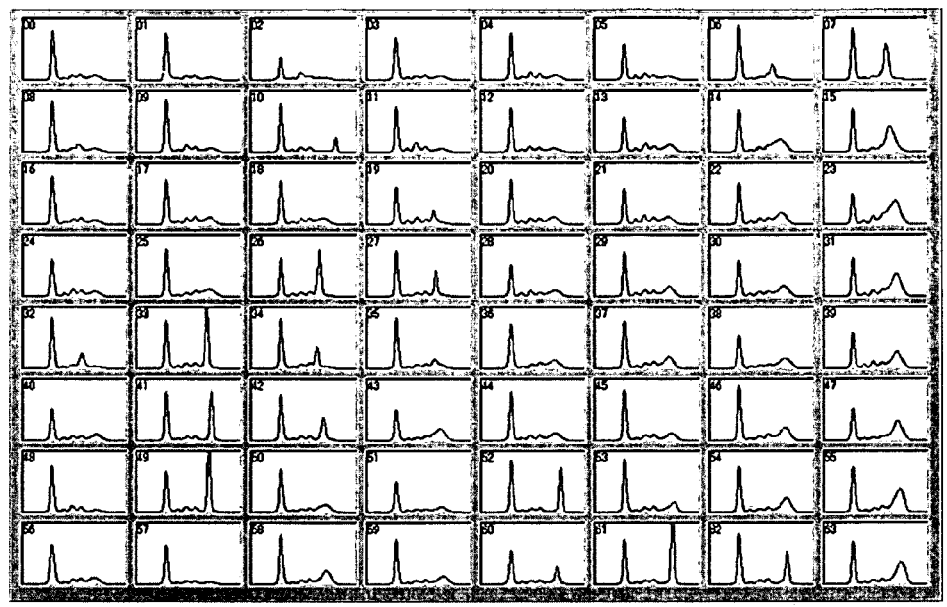
FIG. 9 is an example of a primary class map obtained as a result of primary clustering of protein electrophoretic waveforms using the SOM.
Figure 10:
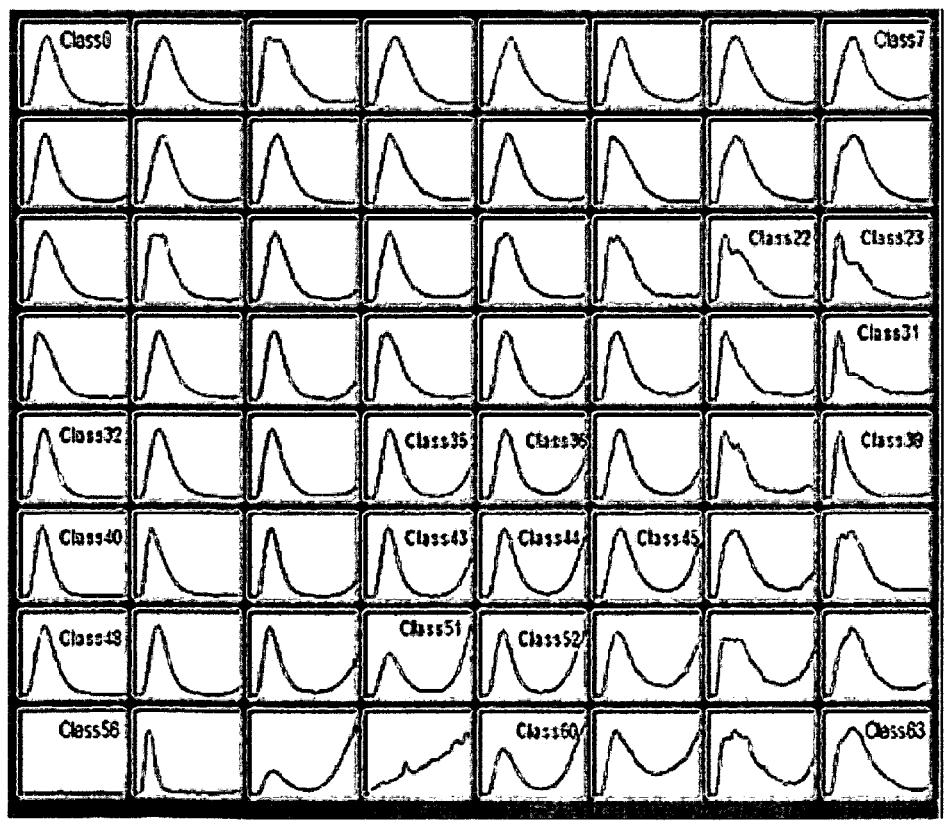
FIG. 10 is an example of a primary class map obtained as a result of primary clustering of blood cell histograms using the SOM.

For example, in the embodiment, the similar-pattern searching apparatus 1 searches the similarities of the leukocyte particle size patterns. However, the similar-pattern searching apparatus 1 can be configured to search similarities of test sample patterns such as one-dimensional protein electrophoretic waveforms and blood cell histograms. The similar-pattern searching apparatus 1 thus can be configured to search the similarities of various types of test sample patterns. In addition, the test sample pattern is not limited to the two-dimensional information such as the leukocyte particle size pattern but can be one-dimensional information or multi-dimensional information (including a time axis). FIG. 9 is an example of a primary class map obtained as a result of allowing the similar-pattern searching apparatus 1 to cluster the protein electrophoretic waveforms using the SOM. FIG. 10 is an example of a primary class map obtained as a result of allowing the similar-pattern searching apparatus 1 to cluster the blood cell histograms using the SOM.

Figure 11:
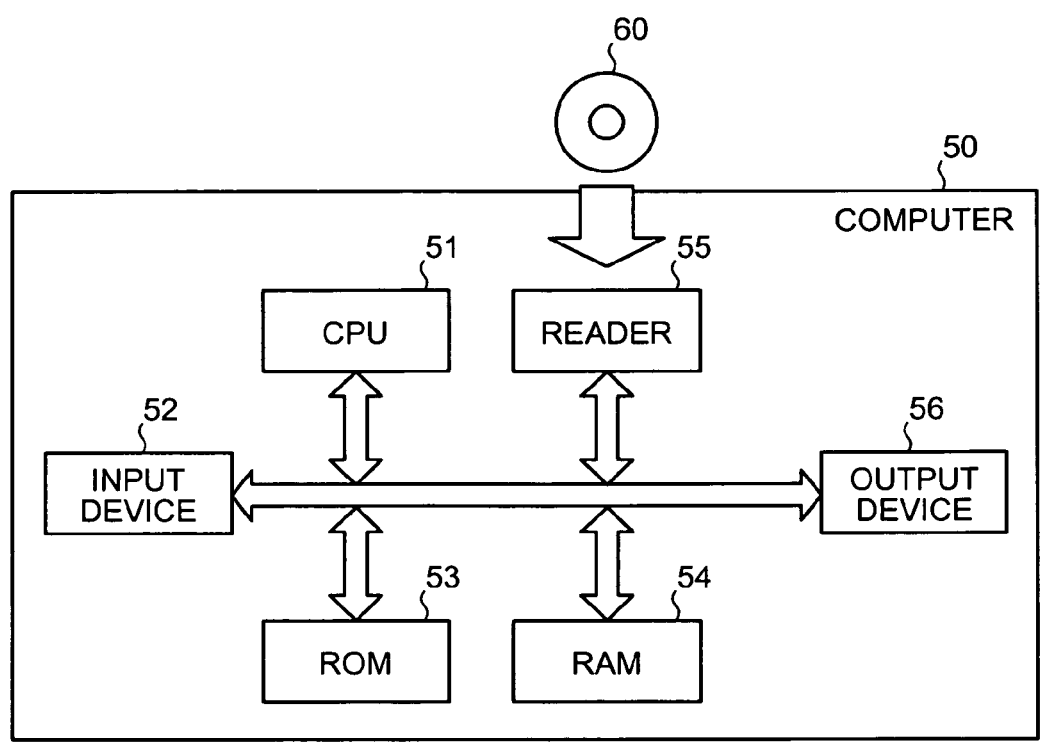
FIG. 11 depicts one embodiment of the present invention.

Furthermore, in the embodiment, a computer program for realizing the functions of the similar-pattern searching apparatus 1 can be recorded in a computer-readable recording medium 60 shown in FIG. 11. In addition, the respective functions of the similar-pattern searching apparatus 1 can be realized by allowing a computer 50 shown in FIG. 11 to read and execute the computer program in the recording medium 60.

The computer 50 shown in FIG. 11 includes a CPU (central processing unit) 51 that executes the computer program, an input device 52 such as a keyboard and a mouse, a ROM (read only memory) 53, a RAM (random access memory) 54 that stores operation parameters and the like, a reader 55 that reads the computer program from the recording medium 60, and an output device 56 such as a display and a printer.

The CPU 51 reads the computer program recorded in the recording medium 60 with the help of the reader 55 and then executes the computer program, thereby realizing the functions of the similar-pattern searching apparatus 1. Examples of the recording medium 60 include an optical disk, a flexible disk, a hard disk, and the like.

INDUSTRIAL APPLICABILITY

As explained so far, the similar-pattern searching apparatus according to the present invention can arbitrarily change the similarity criterion for the similarities with which the respective components are integrated. Therefore, information useful for diagnosis and treatment can be provided.

The invention claimed is:

1. A similar-pattern searching apparatus for searching a pattern having a high similarity to a target pattern of a test sample from a group of patterns including a plurality of patterns, the similar-pattern searching apparatus comprising:
   a storage unit that stores therein a class map generated by selecting model parameters that characterize a plurality of component fractions included in each pattern in the group and by clustering the patterns based on selected model parameters, the model parameters including a number, an average, a variance and a density for the plurality of component fractions; and
   a similar-pattern searching unit that selects a class similar to a component fraction included in the target pattern from the class map in the storage unit, wherein the similar-pattern searching unit that detects the class based on similarity distance from a target class, which is equal to or smaller than a predetermined threshold, and that determines the pattern included in the class as a pattern having a high similarity to the target pattern.

2. The similar-pattern searching apparatus according to claim 1, wherein the patterns are any one of one-dimensional and multi-dimensional.

3. The similar-pattern searching apparatus according to claim 2, wherein the patterns are any one of leukocyte particle size patterns, protein electrophoretic waveforms, and blood cell histograms.

4. A similar-pattern searching method, employed for clinical diagnosis or treatment, of searching a target pattern having a high similarity to a pattern of a test sample from a group of patterns including a plurality of patterns, the similar-pattern searching method comprising:
   in an apparatus for clinical diagnosis or treatment
   generating a class map by selecting model parameters that characterize a plurality of component fractions included in each pattern in the group and by clustering the patterns based on selected model parameters, the model parameters including a number, an average, a variance and a density for the plurality of component fractions;
   storing the class map generated at the generating step into a storage unit; and
   selecting a class similar to a component fraction included in the target pattern from the class map in the storage unit, wherein the selecting includes detecting the class based on similarity distance from a target class, which is equal to or smaller than a predetermined threshold, and determining the pattern included in the class as a pattern having a high similarity to the target pattern.

5. A computer-readable recording medium encoded with a computer program that causes a computer to search a target pattern having a high similarity to a pattern of a test sample from a group of patterns including a plurality of patterns, the computer program causing the computer to execute:
   generating a class map by selecting model parameters that characterize a plurality of component fractions included in each pattern in the group and by clustering the patterns based on selected model parameters, the model parameters including a number, an average, a variance and a density for the plurality of component fractions;
   storing the class map generated at the generating into a storage unit; and
   selecting a class similar to a component fraction included in the target pattern from the class map in the storage unit, wherein the selecting includes detecting the class based on similarity distance from a target class, which is equal to or smaller than a predetermined threshold, and determining the pattern included in the class as a pattern having a high similarity to the target pattern.

6. A similar-pattern searching apparatus for searching a leukocyte particle size pattern having a high similarity to a target leukocyte particle size pattern of a test sample from a group of patterns including a plurality of leukocyte particle size patterns, each of the leukocyte particle size patterns including a plurality of cellular component fractions, the similar-pattern searching apparatus comprising:
   a primary clustering unit that clusters the leukocyte particle size patterns, which are obtained by measurement, in the group while applying a self-organizing map to the leukocyte particle size patterns to thereby generate a primary class map;
   a first-parameter determining unit that executes an EM algorithm for each leukocyte particle size pattern included in the primary class map by using predetermined initial values to thereby determine first-mixture-distribution model parameters including number of cellular components contained in each leukocyte particle size pattern and an average, a variance, and a density of each cellular component;
   a second-parameter determining unit that executes an EM algorithm for each leukocyte particle size pattern in the group by using the first-mixture-distribution model parameters as initial values to thereby determine second mixture distribution model parameters including number of the cellular components contained in each leukocyte particle size pattern, and an average, a variance, and a density of each cellular component;
   a secondary clustering unit that clusters the leukocyte particle size patterns in the group while applying the self-organizing map to the first mixture distribution model parameters to thereby generate a secondary class map;

an inter-class distance master generator that calculates similarity distances between all combinations of the classes included in the secondary class map, and that generates an inter-class distance master that includes a correspondence of each combination of the classes and the similarity distance for the combination;

a storage unit that stores therein the secondary class map and the inter-class distance master;

a class determining unit that determines a target class belonging to each of cellular component fractions included in the target leukocyte particle size pattern from the secondary class map in the storage unit; and a similar-pattern searching unit that detects, as a similar class, a class from the inter-class distance master for which similarity distance from the target class is equal to or smaller than a predetermined threshold, and that determines a leukocyte particle size pattern included in the similar class as a pattern having a high similarity to the target leukocyte particle size pattern.

7. A similar-pattern searching method, employed for clinical diagnosis or treatment, of searching a leukocyte particle size pattern having a high similarity to a target leukocyte particle size pattern of a test sample from a group of patterns including a plurality of leukocyte particle size patterns, each of the leukocyte particle size patterns including a plurality of cellular component fractions, the similar-pattern searching method comprising:

in an apparatus for clinical diagnosis or treatment
clustering the leukocyte particle size patterns, which are obtained by measurement, in the group while applying a self-organizing map to the leukocyte particle size patterns to thereby generate a primary class map;

executing an EM algorithm for each leukocyte particle size pattern included in the primary class map by using predetermined initial values to thereby determine first-mixture-distribution model parameters including number of cellular components contained in each leukocyte particle size pattern and an average, a variance, and a density of each cellular component;

executing an EM algorithm for each leukocyte particle size pattern in the group by using the first-mixture-distribution model parameters as initial values to thereby determine second mixture distribution model parameters including number of the cellular components contained in each leukocyte particle size pattern, and an average, a variance, and a density of each cellular component;

clustering the leukocyte particle size patterns in the group while applying the self-organizing map to the first mixture distribution model parameters to thereby generate a secondary class map;

calculating similarity distances between all combinations of the classes included in the secondary class map, and generating an inter-class distance master that includes a correspondence of each combination of the classes and the similarity distance for the combination;

storing the secondary class map and the inter-class distance master in a storage unit;

determining a target class belonging to each of cellular component fractions included in the target leukocyte particle size pattern from the secondary class map in the storage unit; and detecting, as a similar class, a class from the inter-class distance master for which similarity distance from the target class is equal to or smaller than a predetermined threshold, and determining a leukocyte particle size pattern included in the similar class as a pattern having a high similarity to the target leukocyte particle size pattern.

8. A computer-readable recording medium encoded with a computer program that causes a computer to search a leukocyte particle size pattern having a high similarity to a target leukocyte particle size pattern of a test sample from a group of patterns including a plurality of leukocyte particle size patterns, each of the leukocyte particle size patterns including a plurality of cellular component fractions, the computer program causing the computer to execute:

clustering the leukocyte particle size patterns, which are obtained by measurement, in the group while applying a self-organizing map to the leukocyte particle size patterns to thereby generate a primary class map;

executing an EM algorithm for each leukocyte particle size pattern included in the primary class map by using predetermined initial values to thereby determine first-mixture-distribution model parameters including number of cellular components contained in each leukocyte particle size pattern and an average, a variance, and a density of each cellular component;

executing an EM algorithm for each leukocyte particle size pattern in the group by using the first-mixture-distribution model parameters as initial values to thereby determine second mixture distribution model parameters including number of the cellular components contained in each leukocyte particle size pattern, and an average, a variance, and a density of each cellular component;

clustering the leukocyte particle size patterns in the group while applying the self-organizing map to the first mixture distribution model parameters to thereby generate a secondary class map;

calculating similarity distances between all combinations of the classes included in the secondary class map, and generating an inter-class distance master that includes a correspondence of each combination of the classes and the similarity distance for the combination;

storing the secondary class map and the inter-class distance master in a storage unit;

determining a target class belonging to each of cellular component fractions included in the target leukocyte particle size pattern from the secondary class map in the storage unit; and detecting, as a similar class, a class from the inter-class distance master for which similarity distance from the target class is equal to or smaller than a predetermined threshold, and determining a leukocyte particle size pattern included in the similar class as a pattern having a high similarity to the target leukocyte particle size pattern.

9. A fraction separating apparatus for separating a plurality of cellular component fractions included in a leukocyte particle size pattern, the fraction separating apparatus comprising:

a primary clustering unit that clusters a plurality of leukocyte particle size patterns, which are obtained by measurement, while applying a self-organizing map to the leukocyte particle size pattern to thereby generate a primary class map;

a parameter determining unit that executes an EM algorithm for each leukocyte particle size patterns included in the primary class map by using predetermined initial values to thereby determine mixture distribution model parameters including number of cellular components contained in each leukocyte particle size pattern, and an average, a variance, and a density of each cellular component fraction; and a fraction separating unit that executes an EM algorithm for each leukocyte particle size pattern by using the mixture distribution model parameters as initial values to thereby separate the cellular component fractions included in each leukocyte particle size pattern.

* * * * *